(12) United States Patent
Hickman et al.

(10) Patent No.: US 7,738,963 B2
(45) Date of Patent: Jun. 15, 2010

(54) SYSTEM AND METHOD FOR PROGRAMMING AN IMPLANTABLE PULSE GENERATOR

(75) Inventors: Thomas K. Hickman, Plano, TX (US); Erik D. Engstrom, Murphy, TX (US); Matthew J. Brock, Carrollton, TX (US); John H. Erickson, Plano, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 1116 days.

(21) Appl. No.: 11/359,746

(22) Filed: Feb. 21, 2006

(65) Prior Publication Data

US 2006/0259097 A1    Nov. 16, 2006

Related U.S. Application Data

(63) Continuation-in-part of application No. 11/073,026, filed on Mar. 4, 2005, now Pat. No. 7,254,446, and a continuation-in-part of application No. 11/072,998, filed on Mar. 4, 2005, now Pat. No. 7,295,876.

(60) Provisional application No. 60/550,040, filed on Mar. 4, 2004, provisional application No. 60/550,039, filed on Mar. 4, 2004.

(51) Int. Cl.
*A61N 1/08* (2006.01)
*A61N 1/37* (2006.01)

(52) U.S. Cl. .............................. 607/59; 607/32; 607/60; 607/63

(58) Field of Classification Search .................. 607/117, 607/60, 63, 59, 32, 27
See application file for complete search history.

(56) References Cited

U.S. PATENT DOCUMENTS

| 5,938,690 | A | 8/1999 | Law et al. |
| 6,205,359 | B1 | 3/2001 | Boveja |
| 6,393,325 | B1 * | 5/2002 | Mann et al. .................. 607/46 |
| 6,609,031 | B1 | 8/2003 | Law et al. |
| 7,174,215 | B2 | 2/2007 | Bradley |
| 7,266,412 | B2 | 9/2007 | Stypulkowski |
| 7,489,970 | B2 | 2/2009 | Lee et al. |

\* cited by examiner

*Primary Examiner*—Carl H Layno
*Assistant Examiner*—Natasha N Patel
(74) *Attorney, Agent, or Firm*—Christopher S. L. Crawford; Peter Lando; Melissa Acosta (57) ABSTRACT

In one embodiment, a method of programming an IPG comprises providing one or several GUI screens on the programmer device, the GUI screens comprising a master amplitude GUI control for controlling amplitudes for stimsets of a stimulation program and one or several balancing GUI controls for controlling amplitudes of each stimset of the stimulation program; communicating one or several commands from the programmer device to the IPG to change the amplitude of all stimsets of the stimulation program in response to manipulation of the master amplitude GUI control, wherein the amplitude of each stimulation set is automatically calculated by a level selected through the master amplitude GUI control and one or several calibration parameters for the respective stimulation set; and automatically recalculating the one or several calibration parameters for a respective stimulation set in response to manipulation of one of the balancing GUI controls and storing the recalculated calibration parameters.

9 Claims, 5 Drawing Sheets

SYSTEM AND METHOD FOR PROGRAMMING AN IMPLANTABLE PULSE GENERATOR

CROSS-REFERENCE TO RELATED APPLICATIONS

This application is a continuation-in-part of commonly assigned U.S. patent application Ser. No. 11/073,026, now U.S. Pat. No. 7,254,446, filed Mar. 4, 2005, entitled "SYSTEM AND METHOD FOR STIMULUS CALIBRATION FOR AN IMPLANTABLE PULSE GENERATOR" (which, in turn, claims the benefit of U.S. Provisional Application Ser. No. 60/550,040, filed Mar. 4, 2004, entitled "SYSTEM AND METHOD FOR STIMULUS CALIBRATION FOR AN IMPLANTABLE PULSE GENERATOR") and of U.S. patent application Ser. No. 11/072,998, now U.S. Pat. No. 7,295,876, filed Mar. 4, 2005, entitled "SYSTEM AND METHOD FOR GENERATING AND TESTING TREATMENT PROTOCOLS" (which, in turn, claims the benefit of U.S. Provisional Application Ser. No. 60/550,039 filed Mar. 4, 2004, entitled "SYSTEM AND METHOD FOR GENERATING AND TESTING TREATMENT PROTOCOLS"), all of which are incorporated herein by reference.

TECHNICAL FIELD

The present application is directed, in general, to implantable stimulation devices (e.g., neurostimulators) and programming of implantable stimulation devices.

BACKGROUND

The present application is generally related to stimulation systems, for example, spinal cord, peripheral, deep-brain, and cortical stimulation systems. A spinal cord stimulation system is an implantable pulse generating system used to provide electrical stimulation pulses to an electrode array placed epidurally or surgically near a patient's spine. An implanted pulse generator (IPG) may operate independently to provide the required electrical stimulation, or may interact with an external programmer, which delivers programming, control information, and/or energy for the electrical stimulation, typically through a radio-frequency (RF) or other wireless signal.

Spinal cord stimulation (SCS) is a well accepted clinical method for reducing pain in certain populations of patients. SCS systems typically include an implanted device, lead wires, and electrodes connected to the lead wires. The implanted device receives signals from an external programmer, and transmits corresponding electrical pulses that are delivered to the spinal cord (or other tissue) through the electrodes which are implanted along the dura of the spinal cord. In a typical situation, the attached lead wires exit the epidural space and are tunneled around the torso of the patient to a subcutaneous pocket where the device is implanted.

Spinal cord and other stimulation systems are known in the art. For example, U.S. Pat. No. 3,646,940 discloses an implantable electronic stimulator that provides timed sequenced electrical impulses to a plurality of electrodes so that only one electrode has a voltage applied to it at any given time. Thus, the electrical stimuli provided by the apparatus taught in the '940 patent comprise sequential, or non-overlapping, stimuli.

U.S. Pat. No. 3,724,467 discloses a relatively thin and flexible strip of physiologically inert plastic with a plurality of electrodes formed thereon for stimulation of the spinal cord. The electrodes are connected by leads to an RF receiver, which is also implanted, and which is controlled by an external controller. The implanted RF receiver has no power storage means for generating electrical stimulations and must be coupled to the external controller in order for neurostimulation to occur.

U.S. Pat. No. 3,822,708 discloses another type of electrical spinal cord stimulating device. The device has five aligned electrodes which are positioned longitudinally on the spinal cord and transversely to the nerves entering the spinal cord. Current pulses applied to the electrodes are said to block sensed intractable pain, while allowing passage of other sensations. The stimulation pulses applied to the electrodes are approximately 250 microseconds in width with a repetition rate of 5 to 200 pulses per second. A patient-operable switch allows the patient to change which electrodes are activated, i.e., which electrodes receive the current stimulus, so that the area between the activated electrodes on the spinal cord can be adjusted, as required, to better block the pain.

Other representative patents that show spinal cord stimulation systems or electrodes include U.S. Pat. Nos. 4,338,945; 4,379,462; and 4,793,353. All of the patents noted above are hereby incorporated by reference.

A typical IPG is self contained, having a multi-year battery pack and a single treatment program, and is generally programmed during or immediately following implantation in the patient's body. The battery may be rechargeable or non-rechargeable.

Other SCS systems have no implanted power source, but receive power and programming and/or control information from an external transmitter. These systems will convert the RF signals from the transmitter to provide power to the implanted receiver, and use the RF programming information to determine the intensity, location, and duration of the electrical pulses delivered to the electrodes.

Programming SCS systems is a relatively complicated process. At a high level, programming an SCS system involves selecting stimulation parameters (pulse amplitude, pulse width, pulse frequency, an electrode combination) that are effective in addressing the pain pattern of a patient. In some cases, the patient may experience pain in multiple distinct regions of the patient's body. In such cases, a stimulation "program" can be created to include multiple "stimsets" that are each adapted to address pain in a specific, discrete region of the body.

During an initial or follow-up programming session, stimulation programs may be generated in a somewhat "piecemeal" manner. Specifically, the stimsets are each constructed individually by downloading the stimsets from a patient programmer device to an IPG and observing the response of the patient. The parameters are varied for an individual stimset until a satisfactory stimulation response for a particular region of the patient's body is obtained. Once all of the stimsets are defined in this manner, the stimsets are combined into a stimulation program which is downloaded to the IPG. The stimulation program causes a pulse generator to repeatedly generate pulses in rapid succession according to the respective stimsets. The goal of a stimulation program in SCS is to cause the patient to subjectively experience pain relief for all of the affected regions in a simultaneous manner.

SUMMARY

In one embodiment, a method of programming an implantable pulse generator (IPG), comprises providing one or several graphical user interface (GUI) screens on the programmer device, the one or several user interface screens comprising (i) a master amplitude GUI control for controlling amplitudes for multiple stimsets of a stimulation program and (ii) one or several balancing GUI controls for controlling amplitudes of each individual stimset of the stimulation program; communicating one or several commands from the programmer device to the IPG to change the amplitude of all stimsets of the stimulation program in response to manipulation of the master amplitude GUI control by a user of the programmer device, wherein the amplitude of each stimulation set is automatically calculated by a level selected through the master amplitude GUI control and one or several calibration parameters for the respective stimulation set; and automatically recalculating the one or several calibration parameters for a respective stimulation set in response to manipulation of one of the balancing GUI controls by the user and storing the recalculated one or several calibration parameters to affect a change in amplitude for the respective stimulation set.

In another embodiment, a method of programming an implantable pulse generator (IPG), comprises providing a plurality of stimsets for a stimulation program for execution by the IPG; executing the stimulation program by the IPG; providing one or several graphical user interface (GUI) screens on a programmer device, the one or several GUI screens comprising one or several GUI controls for controlling a respective stimulation amplitude associated with each stimset of the stimulation program; and communicating one or several commands from the programmer device to the IPG to change the amplitude of a respective stimset in response to manipulation of one GUI control of the one or several GUI controls, wherein the one or several commands are communicated while the IPG is executing the stimulation program and the IPG changes the amplitude of the respective stimset without the patient sensing interruption of the execution of the stimulation program.

The foregoing has outlined rather broadly certain features and/or technical advantages in order that the detailed description that follows may be better understood. Additional features and/or advantages will be described hereinafter. It should be appreciated by those skilled in the art that the conception and specific embodiments disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

In some representative embodiments, there are systems and methods for calibrating and/or programming a stimulation device such as, for example, an implantable pulse generator (IPG). The IPG, whether it is a self-contained implantable pulse generator (SCIPG) or externally-powered implantable pulse generator (EPIPG), communicates with an external programmer to determine the characteristics of the stimuli to be delivered to the lead electrodes. In representative embodiments, the IPG provides stimulation using a "multi-stimset" program. That is, the IPG repeatedly cycles through multiple stimsets that define stimulation parameters. As the IPG cycles through the stimsets, the IPG generates pulses according to the pulse characteristics in the stimsets and delivers the pulses to respective electrodes defined by the stimsets. By delivering pulses according to a multi-stimset program, representative embodiments enable relatively complex pain patterns to be treated in a patient.

As used herein, an SCIPG is an IPG having an implanted power source, such as a long-lasting or rechargeable battery. An EPIPG is an IPG which receives at least some of its operating power from an external power transmitter, preferably in the form of a RF signal. The external power transmitter, in the preferred embodiment, is built into the external programmer.

Figure 1:
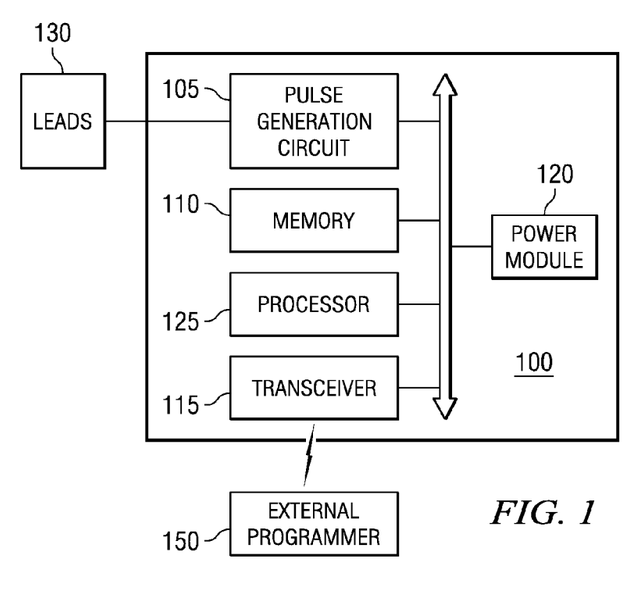
FIG. 1 depicts a block diagram of an implantable pulse generator according to one representative embodiment.

FIG. 1 depicts a diagram of the components of an IPG 100 in accordance with the preferred embodiment. The implanted device comprises, but is not limited to, a pulse generation circuit 105, a non-volatile memory 110, a transceiver 115, a power module 120, and a processor 125. Memory 110 may also include volatile memory (not shown).

In an SCIPG, the power module 120 will include a long-term battery or a rechargeable battery and a voltage detection, and regulation circuit. In an EPIPG, and in an SCIPG with a rechargeable battery, the power module 120 will include a circuit for converting radio-frequency (RF) energy (or other energy) into direct current. In either case, the power module 120 is connected to power the processor 125 and the pulse generation circuit 105.

The pulse generation circuit 105 is connected to receive power from power module 120 and to be controlled by processor 125. Processor 125 is connected to receive power from power module 120 and to read from, and write to, non-volatile memory 110. Further, processor 125 is connected to receive and decode data from transceiver 115. Note that in different embodiments, transceiver 115 may only be a receiver, while in preferred embodiments, processor 125 is connected to also transmit data via transceiver 115. Further, in various embodiments, transceiver 115 receives power signals for operating or recharging the IPG, transmits, and receives.

Transceiver 115 is positioned to receive RF commands from an external programmer 150, and to deliver these commands to processor 125. Further, in an EPIPG, the receiver 115 is configured to receive RF power signals, and to deliver these to power module 120.

Non-volatile memory 110 contains programming and control data, and can be written to and read from by processor 125.

Leads 130 are implanted in the patient's epidural space (or other locations), as described above or known to those of skill in the art. Leads 130 connect with pulse generation circuit 105, optionally via lead extensions (not shown).

Leads 130, in one embodiment, have multiple electrodes, each of which can be independently controlled by the pulse generation circuit 105. Each electrode can be individually set as a positive state (acting as an anode), a negative state (acting as a cathode), or to a high impedance (turned off). The pulse generation circuit 105, under control of the processor 125, also controls the pulse amplitude, pulse width, and pulse frequency to each electrode on the leads 130.

Also shown here (although not a part of the IPG 100 itself) is external programmer 150 which communicates with transceiver 115 of IPG 100. External programmer 150 can be either an external patient programmer (EPP), which is typically carried and operated by the patient, or an advanced programmer, which is typically operated by the patient's physician or clinician. External programmer 150 will typically communicate with transceiver 115 via an antenna (not shown), placed on or near the patient's body proximal to the IPG 100, via near-field or far-field technology.

In some representative embodiments, processor 110 executes software code that responds to programming data and commands communicated from external programmer 150 to define one or several multistim programs that are effective in addressing a patient's pain pattern. Specifically, external programmer 150 preferably communicates "stimsets" and "programs" to be stored in memory 110. External programmer 150 also communicates commands to begin stimulation according to one of the programs stored in memory 110. Processor 125 processes the command and causes pulse generation circuit 105 to repeatedly cycle through the stimsets of the selected program. As pulse generation circuit 105 cycles through the stimsets, pulse generation circuit 105 generates pulses according to the pulse characteristics in the stimsets and delivers the pulses to respective electrodes of lead(s) 130 defined by the stimsets.

In preferred embodiments, commands can be sent to control which stimsets in a program are active during a portion of the test process. In such a case, only pulses are generated for the "active" stimsets and the "inactive" stimsets are temporarily ignored for the purpose of pulse generation. Also, external programmer 150 can communicate a command to modify the amplitude of one of the stimsets as the selected program is executed or run by pulse generation circuit 105 as discussed in U.S. patent Ser. No. 11/072,998, entitled "SYSTEM AND METHOD FOR GENERATING AND TESTING TREATMENT PROTOCOLS." That is, upon receiving the updated amplitude information for the respective stimset, processor 125 updates the amplitude setting associated with the selected stimset. Pulse generation circuit 105 uses the updated amplitude information upon the next stimulation cycle and need not cease stimulation pulses during the update communication process. Accordingly, amplitude programming can occur in real-time as stimulation is applied by the IPG.

Figure 7:
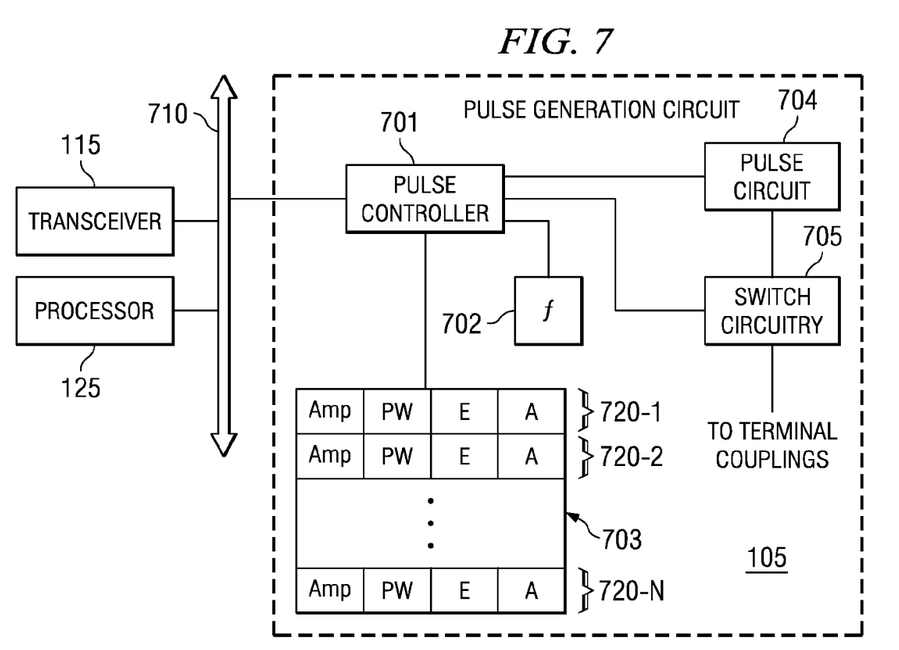
FIG. 7 depicts pulse generation circuit 105 that is useful to facilitating real-time control of the amplitude and activate state of stimsets while a program is being executed according to one representative embodiment.

FIG. 7 depicts pulse generation circuit 105 that is useful for facilitating real-time control of the amplitude and activate state of stimsets while a program is being executed according to one representative embodiment. Within pulse generation circuit 105, pulse circuit 704 comprises the active components that generate a pulse upon command. The active components are configurable to control the amplitude of the generated pulse. The generated pulse is controllably deliverable to specific electrodes on leads 130 (shown in FIG. 1) using switch circuitry 705. Switch circuitry 705 allows each electrode of leads 130 to be set to a high impedance state, a positive polarity, or a negative polarity.

Pulse controller 701 controls the amplitude of the active circuitry, the state of switch circuitry 705, the pulse timing, and the pulse width to allow execution of a stimulation program. The frequency of repetition of the stimulation program is defined by the value stored in register 702. Register file 703 comprises the parameters for a plurality of stimsets 720-1 through 720-N. Stimsets 720 include a pulse amplitude value ("Amp"), a pulse width value ("PW"), and electrode configuration ("E"), and an activate/inactive state value ("A").

During execution of the program defined by stimsets 720, pulse controller 701 begins a program cycle by first examining stimset 720-1. Pulse controller 701 determines whether the stimset's 720 "A" value is set to the active or inactive state. If the value is set to the inactive state, pulse controller 701 skips to the next stimset (i.e., no pulse is generated for an "inactive" stimset). If the value is set to the active state, pulse controller 701 configures the active components of pulse circuit 704 to generate a pulse of an amplitude defined by the "Amp" value. Also, pulse controller 701 configures switch circuitry 705 according to the electrode configuration defined by the "E" configuration parameter defined in the stimset 720. Then, pulse controller 701 asserts a "fire" signal to pulse circuit 704 that causes pulse circuit 704 to output a waveform (e.g., a constant voltage or constant current waveform) of the defined amplitude and that is delivered through switch circuitry 705. Pulse controller 701 continues to assert the "fire" signal for the amount of time defined by the pulse width "PW" parameter of the stimset 720 and pulse circuitry 704 continues outputting the waveform.

After the time defined by the pulse width "PW" parameter is completed, pulse controller 701 ceases assertion of the "fire" signal and waits a relatively short predetermined amount of time. Pulse controller 701 then goes to the next stimset 720 and repeats this procedure until pulse controller 701 reaches the last stimset 720-N. Upon completion of the last stimset 720-N, pulse controller 701 waits an amount of time defined by the frequency stored in register 702. The frequency stored in register 702 defines the frequency with which the stimulation program is repeated.

The stimset parameters can be changed in real-time as the stimulation program is being executed by pulse generation circuit 705. Specifically, processor 125 executes software that responds to programming commands received via transceiver 115. When a command is processed by the software, processor 125 communicates a suitable signal through bus 710 to pulse controller 701. The signal identifies the stimset 720 to be modified and the suitable values. Pulse controller 701 overwrites the appropriate values in register file 703. The next time that pulse controller 701 access the modified stimset 720, the new parameter values are employed for the pulse generation/delivery. Also, pulse controller 702 need not cease execution of the stimulation program. Accordingly, modification of one or several stimsets can occur in real-time as other stimsets are being executed and the patient response can be observed.

Figure 2:
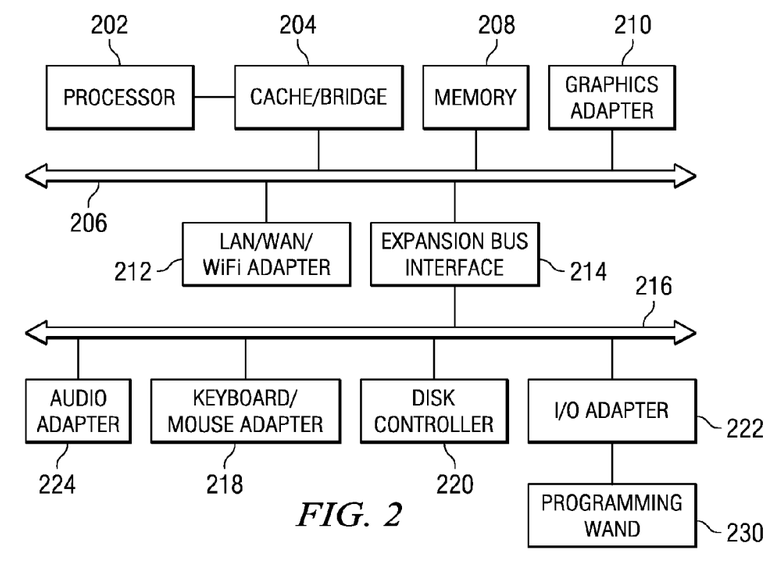
FIG. 2 depicts a block diagram of a data processing system for use as an IPG programmer device according to one representative embodiment.

FIG. 2 depicts a data processing system in which a preferred embodiment for use as an external programmer. The depicted data processing system includes a processor 202 connected to a level two cache/bridge 204, which is connected in turn to a local system bus 206. Local system bus 206 may be, for example, a peripheral component interconnect (PCI) architecture bus. Also connected to local system bus in the depicted example are a main memory 208 and a graphics adapter 210.

Other peripherals, such as local area network (LAN)/Wide Area Network (WAN)/Wireless (e.g., WiFi) adapter 212, may also be connected to local system bus 206. Expansion bus interface 214 connects local system bus 206 to input/output (I/O) bus 216. I/O bus 216 is connected to keyboard, mouse adapter, or other input device 218, disk controller 220, and I/O adapter 222.

Also connected to I/O bus 216 in the example shown is audio adapter 224, to which speakers (not shown) may be connected for playing sounds. Keyboard/mouse adapter 218 provides a connection for a pointing device (not shown), such as a mouse, trackball, trackpointer, pen, etc.

Connected to the I/O adapter 222 is programming wand 230. Programming wand 230 is used to communicate with an IPG as shown in FIG. 1, in the manner and for the functions described herein. In other embodiments, the I/O adapter 222 is connected to communicate with an IPG.

Those of ordinary skill in the art will appreciate that the hardware depicted in FIG. 2 may vary. For example, other peripheral devices, such as an optical disk drive and the like, also may be used in addition or in place of the hardware depicted. The depicted example is provided for the purpose of explanation only and is not meant to imply architectural limitations with respect to the present invention.

A data processing system in accordance with a preferred embodiment of the present invention includes an operating system employing a graphical user interface. The operating system permits multiple display windows to be presented in the graphical user interface simultaneously, with each display window providing an interface to a different application or to a different instance of the same application. A cursor in the graphical user interface may be manipulated by a user through the pointing device. The position of the cursor may be changed and/or an event, such as clicking a mouse button, generated to actuate a desired response.

One of various commercial operating systems, such as a version of Microsoft Windows® a product of Microsoft Corporation located in Redmond, Wash. may be employed if suitably modified in accordance with the present invention as described.

In a conventional EPIPG, the external programmer is used to send both a power signal and pulse-generation instructions, on a real-time basis, to the EPIPG. In this case, the programming for the EPIPG is stored on the external programmer.

A program consists of one or more stimulation settings, also referred to herein as "stimsets." The programmed stimulation settings specifically define and characterize the administered electric pulse stimulation. Other information related to stimulation settings, applications, and pain management, not necessary for an understanding of the presently preferred embodiments, is found in U.S. Pat. No. 5,938,690, filed 7 Jun. 1996 and issued 17 Aug. 1999, U.S. Pat. No. 6,609,031, filed 7 Jun. 1996 and issued 19 Aug. 2003, and U.S. patent application Ser. No. 10/120,953, filed 11 Apr. 2002 and published 22 Aug. 2002 as United States Patent Application Publication No. 2002/0116036, all of which are hereby incorporated by reference.

In one embodiment, each stimset is comprised of an electrode configuration and stimulation amplitude, stimulation frequency, and/or stimulation pulse width, and those of skill in the art will recognize that other parameters can be included. The electrode configuration defines whether each electrode is on or off and, if on, the polarity of that electrode. The amplitude is the intensity of the applied electric pulse. The frequency is the number of times the electrodes are turned on each second. The pulse width is the amount of time the pulse is left on during each cycle.

A program is defined as having at least one stimset, and generally corresponds to providing a treatment relating to a specific part of a patient's body. A program can have multiple stimsets; in this case, each stimset is applied sequentially, repeatedly, and/or randomly. Preferably, each program is applied so that the patient experiences the combined effect of each stimset, as if they were being applied simultaneously.

For example, a first stimset may provide relief to a patient's right leg, and a second stimset may provide relief to a patient's left leg. According to one embodiment, then, there will be at least three programs stored in the patient's programmer:

Program 1 comprises the first stimset;

Program 2 comprises the second stimset; and

Program 3 comprises both the first and second stimsets.

In this case, when the patient uses program 1 on the IPG, she would feel relief in her right leg, program 2 would provide relief in her left leg, and program 3 would provide relief in both legs.

A program comprising more than one stimset is referred to herein as a "multistim program."

In one embodiment, the programmer is capable of storing up to 24 different programs, each program having up to 8 stimsets. Of course, in other embodiments, the programmer can store a much greater number of programs, each having associated a much greater number of stimsets. In certain embodiments, the IPG itself can store various numbers of programs having varying numbers of stimsets.

In the preferred embodiment, all active electrodes in a stimset receive the same stimulation input, including the same pulse width, pulse frequency, and pulse amplitude. Each electrode in the stimset is assigned a polarity of positive, negative, or off. For example, a first stimset for an 8-electrode lead can be defined as having an amplitude of approximately 4 mA, delivered with a 280 microsecond pulse width and an 80 Hz frequency, with the following electrode polarities, with "+" indicating a positive polarity (anode), "−" indicating a negative polarity (cathode), and "0" indicates that the electrode is off:

|  | Electrode # | | | | | | | |
| --- | --- | --- | --- | --- | --- | --- | --- | --- |
|  | 0 | 1 | 2 | 3 | 4 | 5 | 6 | 7 |
| Polarity | + | + | 0 | 0 | − | − | + | 0 |

Note that in the preferred embodiment, every stimset must have at least one anode and one cathode. In an alternate embodiment, the IPG itself can act as an anode. A second stimset for an 8-electrode lead can be defined as having an amplitude of approximately at 4.2 mA, delivered with a 240 microsecond pulse width and an 80 Hz frequency, with the following electrode polarities:

|  | Electrode # | | | | | | | |
| --- | --- | --- | --- | --- | --- | --- | --- | --- |
|  | 0 | 1 | 2 | 3 | 4 | 5 | 6 | 7 |
| Polarity | − | − | 0 | + | − | 0 | + | 0 |

Then, if a multistim program contains both the first and second stimset (as in the exemplary Program 3, above), the IPG will rapidly alternate between the first and second stimsets, so that the patient experiences the combined effect of both stimsets in the multistim program. In a preferred embodiment, all stimsets in a program have the same frequency, but other embodiments allow for different frequencies in a single program.

A typical pulse, in a preferred embodiment, is approximately 4V-5V at 4 mA, delivered with a 280 microsecond pulse width and an 80 Hz frequency. Those of skill in the art will recognize that the pulse can be delivered as constant current pulse or a constant voltage pulse (or in any other suitable manner).

Figure 3:
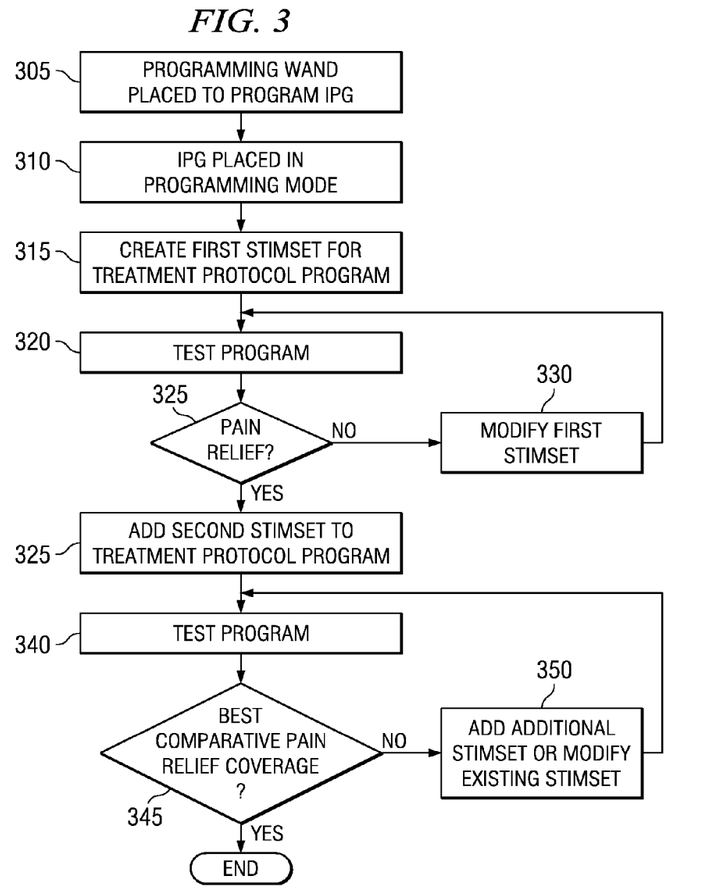
FIG. 3 depicts a flowchart of a process for programming the IPG with multiple treatment-protocol programs according to one representative embodiment.

FIG. 3 depicts a flowchart of a process for programming the IPG with multiple treatment-protocol programs. Note that this process is used to program an already-implanted IPG; a similar process can be used to pre-program the IPG before implantation.

This process is typically performed by a physician or other professional using an advanced programmer, as described herein. Generally, this programming process is not one that would normally be performed by a patient, but could be so if the patient were properly trained.

First, a programming wand will be placed in a location proximate to the IPG or the IPG antenna (step 305). In other embodiments, "far-field" programming can be used. Next, preferably using an RF signal, the advanced programmer will place the IPG into programming mode (step 310).

The advanced programmer is then used to create a stimset for a treatment protocol program (step 315). The treatment protocol program may be stored in either the IPG or the programmer in certain embodiments of the invention. This program is tested (step 320), and the patient will report whether she is experiencing any pain relief from the stimulation (step 325). If not, the first stimset is modified and the program comprising the modified stimset is tested (step 330, returning to step 320).

If the patient does experience relief, the programmer will then select a second stimset (step 335) for the program, and test the program in step 340. The first and second stimset are alternately used by the tested program in preferred embodiments of the invention. In other embodiments, the first and second stimset are used in rapid succession either randomly or sequentially by the IPG to generate stimulation in step 340. This enables the IPG to treat "complex" pain in multiple body areas, as each stimset in the tested program can cover a different body area, or can overlap for more complete coverage in a specific area.

In the preferred embodiment, the tested program comprising a first and a second stimset is sent to the IPG and executed. A decision is then made in step 345 by receiving a patient selection as to whether the tested program provides the best comparative pain relief. If the tested program does not provide the best comparative pain relief, then additional stimsets are added to the program or existing stimsets are modified in step 350. Stimsets can be selectively activated and deactivated. The addition, modification, activation, and/or deactivation of stimsets preferably occur while the program is being executed by the IPG and testing continues as before in step 340. In certain embodiments, more than one program is generated by the process described above, and the separate programs are compared to each other. Steps 335-350 continue until an acceptable program is generated.

Note that, optionally, the new secondary stimset in the test multistim program can either replace one of the stimsets in the program, or can be added as an additional stimset in the test multistim program. Thus, the test multistim program can include as few as two stimsets up to as many as eight stimsets, in the preferred embodiment, or even more in alternate embodiments. Of course, a program can consist of only one stimset, but then it is not an actual "multistim" program.

According to the process above, a multistim treatment program can be quickly developed using a technique similar to the process used in determining an eyeglass prescription. A series of tests are made wherein the "best-so-far" multistim program is compared against a test multistim program, and the patient merely has to indicate which of the two feels better. The better of the two is stored, and used against a new test multistim program in the subsequent comparison.

Here, the test multistim programs can be individually programmed by the operator of the programmer, or can be automatically generated by the programmer. In either case, the operator will simply indicate whether program "A" or program "B" is selected as the new "best-so-far" multistim program, according to the patient's feedback.

When the patient indicates that full-coverage relief has been achieved, or the operator otherwise determines that the best practical coverage has been achieved, the process will end and the current "best-so-far" or known-good program is stored to the patient's IPG.

Figure 4:
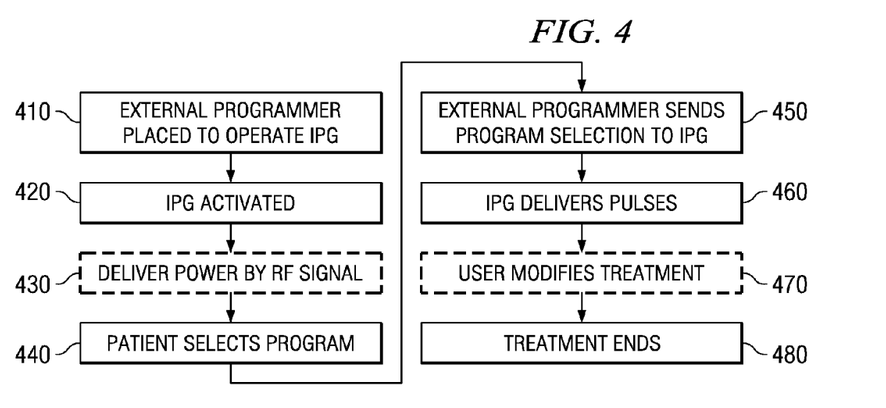
FIG. 4 depicts a flowchart for adjusting the amplitude associated with a stimset in real-time as a multistim set program is being executed by an IPG according to one representative embodiment.

FIG. 4 depicts a flowchart that describes the use of an IPG having multiple treatment-protocol programs stored therein. This process can be performed by a clinician during IPG programming or can be performed by the patient to respond to the variations in the intensity of pain at different bodily locations.

First, the external programmer will be placed in a location proximate to the IPG or the IPG antenna (step 410). Next, preferably using an RF signal, the advanced programmer will activate the IPG (step 420).

During operation, the external programmer will optionally, as in the case of an EPIPG, supply power to the IPG, preferably using an RF signal (step 430). The patient will select the treatment protocol on the external programmer (step 440), and the external programmer will send an RF signal to the IPG to indicate the selected treatment-protocol program (step 450). Alternatively, if a treatment protocol selection is not sent by the external programmer, the IPG will select one of the stored treatment-protocol programs as the "default" program.

The IPG delivers the pulse stimuli, as described herein, according to the selected treatment-protocol program (step 460) and its associated stimsets. The user can modify the amplitude or other aspects of the treatment as needed, using the external programmer (step 470). The amplitude or other pulse characteristics for a given stimset in a multi-stimset program can occur in real-time as the program is being executed.

When the programming/testing is completed, or when the user chooses, the pulse-stimulus ends (step 480).

Calibration of an IPG is another process that typically occurs during IPG programming. Calibration of an IPG is important, because application of the pulses using the same absolute amplitude to different electrode combinations can result in the patient subjectively experiencing different amounts of stimulation. That is, the stimulation experienced by the patient in association with one region of the patient's body can be significantly stronger than the stimulation experienced in association with another region of the patient's body. Accordingly, it is desirable to account for such variations for multistim programs.

Calibration of an IPG typically occurs by determining one or several subjective stimulation levels. As disclosed in U.S. patent Ser. No. 11/073,026, entitled "SYSTEM AND METHOD FOR STIMULUS CALIBRATION FOR AN IMPLANTABLE PULSE GENERATOR," subjective stimulation levels for an IPG can include a "perception threshold level" (PV), a "comfort level" (CV), and a "maximum tolerable level" (MTV). The perception threshold level refers to the amplitude level that is minimally required for the patient to sense stimulation for a given electrode combination. Comfort level refers to the amplitude level that is most comfortable for a patient under ordinary conditions. The maximum tolerable level refers to the highest amplitude level that is acceptable for the patient without the patient experiencing undue discomfort from the stimulation.

By determining these values, a GUI or other interface for a programmer device can operate according to a more intuitive manner of operation. Specifically, an "amplitude" GUI control can specify a range of selectable amplitude values (e.g., 20 different values) in a simplified form (e.g., in a "ramp" GUI control). When the GUI control is manipulated, the actual applied amplitudes are mapped from the selected value from the GUI control to a value within a range defined by the calibrated PV, CV, and MTV values. For example, if the ramp GUI control is at the lowest position, stimulation is applied at a level equal to the PV calibration parameter(s). If the ramp GUI control is positioned at its middle position, stimulation is applied at a level equal to the CV calibration parameter(s). If the ramp GUI control is positioned at its highest position, stimulation is applied at a level equal to the MTV calibration parameter(s). In a multi-stimset program, when a master amplitude GUI control is used, the actual applied amplitude for each stimset can be different. Specifically, the applied amplitude of each stimset is defined by the level of the master amplitude GUI control and the calibration values (e.g., the PV, CV, MTV values) associated with the respective stimset.

One issue associated with using calibration levels and multiple stimsets in a program is the subjective experience of the stimulation in the distinct regions of the body may actually change when the stimsets are used in a multi-stimset format to create a stimulation program. It is not known exactly why combining multiple stimsets can cause a change in the stimulation experience. Nonetheless, it is believed that during the rapid delivery of stimulation pulses, an initial pulse according to a first stimset can cause some degree of nerve polarization or hyperpolarization that affects the degree of stimulation caused by a successive pulse according to a second stimset in the same program.

Figure 5:
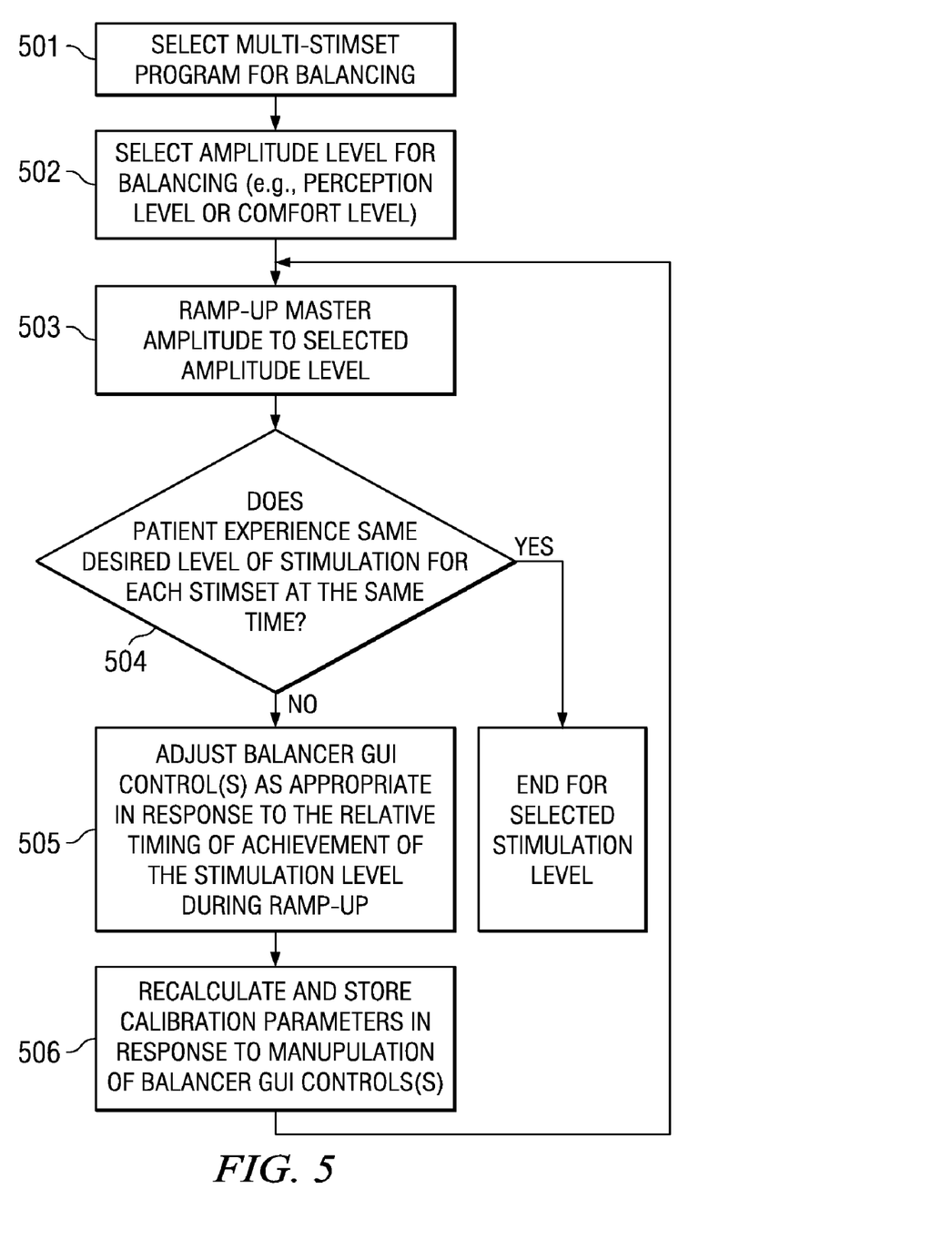
FIG. 5 depicts a flowchart for balancing calibration parameters of stimsets in a multi-stimset program according to one representative embodiment.

FIG. 5 depicts a flowchart for balancing amplitude levels of a multistim program in accordance with one representative embodiment. This process is preferably performed using an advanced programmer by a physician or another trained practitioner, although a patient could perform the process. The user interface screens, GUI elements, and calculation functionality on the advanced programmer discussed in regard to FIG. 5 is preferably implemented in software code (e.g., within an IPG programming software application).

First, a multi-stimset program is selected for balancing (step 501). As described above, the multi-stimset program comprises a plurality of stimulation settings (stimsets) that are applied in sequence in a repeated manner when executed by an IPG.

Figure 6A:
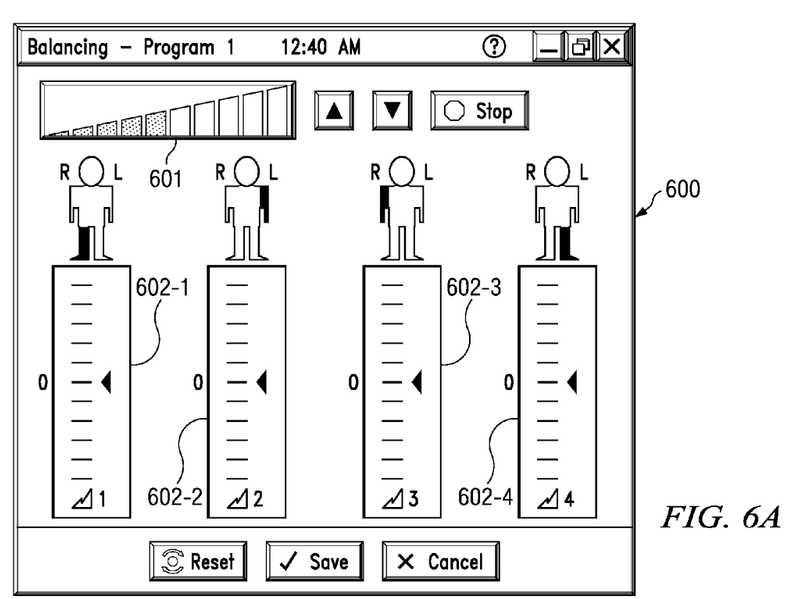
FIGS. 6A and 6B depict GUI screens for balancing calibration parameters of stimsets in a multi-stimset program according to one representative embodiment.

A suitable GUI element on an advanced programmer is used to select a "master" amplitude value corresponding to one of the calibration levels for balancing (step 502). FIG. 6A depicts GUI screen 600 containing amplitude control 601 for setting a master amplitude value according to one representative embodiment.

A ramp-up procedure is initiated by the advanced programmer for the stimulation program (step 503). In the ramp-up procedure, the stimulation program is executed by the IPG and the amplitude for each stimset is gradually brought up to the respective value of the calibration parameter being calibrated. For example, in one stage of the balancing process, the amplitude for each stimset is gradually raised to the value defined by the stimset's respective CV parameter.

Figure 6B:
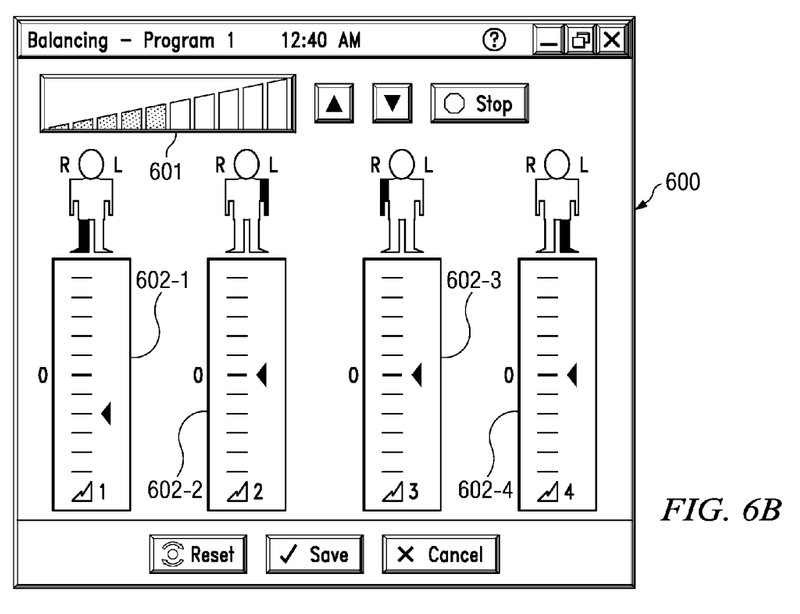

Feedback is obtained from the patient regarding whether the desired level of stimulation for each stimset was initially experienced at the same time (step 504). If the desired level of stimulation was reached at substantially the same time for all stimsets, no (further) balancing need occur. If not, one or several other GUI elements (e.g., in a set of "balancer" GUI elements) provided by the advanced programmer can be manipulated in relation to the order in which the stimulation was experienced (step 505). For example, if the comfort level for a first stimset preceded the comfort level for a second stimset, the "balancer" bar associated with the first stimset could be manipulated "downward," as shown in FIG. 6B, to reduce the stimset's calibration parameter and, hence, amplitude. Bar GUI controls 602-1 through 602-4 in balancing screen 600 are associated with respective stimsets to enable balancing to occur between the stimsets.

Upon the basis of the manipulation of the balancer GUI elements, the associated calibration parameters are recalculated and stored (step 506). In the example given above, the CV parameter for the first stimset would be decreased in response to the manipulation of the balancer bar element for that stimset. The balancing process returns to step 503 to verify that the newly adjusted CV parameter(s) is/are correct. Also, it is noted that a subset of MTV parameters can be calculated in terms of the PV and CV values and are not directly determined. In one embodiment, the subset of MTV parameters for a stimset equals (2*CV−PV). Accordingly, whenever a change to either the PV parameters or the CV parameters occurs, the MTV parameters are preferably recalculated.

Once a given type of calibration parameters are balanced, any other set of calibration parameters could be similarly balanced.

When all of the calibration parameters of the stimsets of a program are balanced, a master amplitude control of stimulation causes the patient to experience uniform stimulation levels in the various bodily regions affected by the stimsets. For example, as a user initially ramps up stimulation, the patient will initially perceive stimulation in each bodily region at the same time. Also, as the patient chooses to increase the amplitude using the master amplitude GUI control, the stimulation will subjectively increase in an even manner across all the affected bodily regions.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 U.S.C. §112 unless the exact words "means for" are followed by a participle.

It may be advantageous to set forth definitions of certain words or phrases used throughout this patent document: the terms "include" and "comprise," as well as derivatives thereof, mean inclusion without limitation; the term "or" is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and if the term "controller" is utilized herein, it means any device, system or part thereof that controls at least one operation, whether such a device is implemented in hardware, firmware, software or some combination of at least two of the same. It should be noted that the functionality associated with any particular controller may be centralized or distributed, whether locally or remotely.

What is claimed is:

1. A method of programming an implantable pulse generator (IPG), comprising:
   providing a graphical user interface (GUI) screen on a programmer device, the GUI screen comprising (i) a master amplitude GUI control for selecting a master amplitude value from a plurality of amplitude values for a stimulation program comprising multiple stimsets, wherein each stimset comprises first, second, and third amplitude calibration parameters and an electrode configuration and (ii) multiple balancing GUI controls where each balancing GUI control directly controls the first amplitude calibration parameter for a corresponding stimset of the stimulation program;
   communicating one or more commands from the programmer device to the IPG to change the amplitudes of generated pulses for all stimsets of the stimulation program in response to manipulation of the master amplitude GUI control by a user of the programmer device, wherein the amplitude of each stimulation set is automatically calculated by a selected master amplitude value from the plurality of amplitude values and the first, second, and third amplitude calibration parameters of the respective stimulation set;
   automatically recalculating amplitude calibration parameters of a stimset corresponding to a manipulated balancing GUI control, the first amplitude calibration parameter of the stimset being assigned a value in direct relation to a level of the manipulated balancing GUI control, the second amplitude calibration parameter of the stimset being assigned a value as a function of the recalculated first amplitude calibration parameter and the third amplitude calibration parameter; and
   communicating one or more commands from the programmer device to the IPG to change the amplitude for pulses generated for a respective stimset of the stimulation program in response to recalculation of amplitude calibration parameters for the respective stimset.

2. The method of claim 1 wherein the IPG substantially continuously applies stimulation by generating and delivering pulses in sequence and in a repeating manner according to the stimsets of the stimulation program over multiple modifications of the master amplitude GUI control and of one or more of the multiple balancing GUI controls.

3. The method of claim 2 wherein during the ramp-up procedure, the amplitude for pulses for each stimset is gradually increased to the amplitude value corresponding to a stimulation level at which a patient initially experiences a stimulation effect for the electrode configuration in the respective stimset.

4. The method of claim 1 wherein the GUI screen depicts a respective, distinct bodily region affected by the corresponding stimset for each of the balancing GUI controls.

5. The method of claim 4 wherein during the ramp-up procedure, the amplitude for pulses for each stimset is gradually increased to the amplitude value corresponding to a stimulation level at which a patient experiences a comfortable stimulation effect for the electrode configuration in the respective stimset.

6. The method of claim 1 further comprising:
   automatically ramping amplitudes of pulses generated by the IPG for all stimsets of the stimulation program.

7. The method of claim 1 wherein the amplitude calibration parameter of a respective stimset stores an amplitude value corresponding to a stimulation level at which a patient initially experiences a stimulation effect for the electrode configuration in the respective stimset.

8. The method of claim 1 wherein the amplitude calibration parameter of a respective stimset stores an amplitude value corresponding to a stimulation level at which a patient experiences a comfortable stimulation effect for the electrode configuration in the respective stimset.

9. A method of programming an implantable pulse generator (IPG), comprising:
   (i) operating a programming device to provide a graphical user interface (GUI) screen, the GUI screen comprising (i) a master amplitude GUI control for controlling a single master amplitude of a stimulation program, the stimulation program comprising multiple stimsets that each comprise a respective electrode configuration and an amplitude calibration parameter and (ii) multiple balancing GUI controls where each balancing GUI control controls the respective amplitude calibration parameter of a corresponding individual stimset of the stimulation program;
   (ii) initiating a ramp-up procedure on the programmer device including communicating one or several commands from the programmer device to the IPG, wherein during the ramp-up procedure: (A) the IPG generates stimulation pulses in sequence in a repeating manner for each stimset of the stimulation program, wherein the amplitude for pulses for each stimset is determined using at least the amplitude calibration parameter of each stimset, and wherein the stimulation program is adapted to treat pain of the patient in at least two separate bodily regions, and (B) the amplitude of pulses for each stimset of the stimulation program is gradually increased;
   (iii) receiving feedback from the patient regarding whether the patient experienced a stimulation sensation first in one of the at least two separate bodily regions during the ramp-up procedure;
   (iv) manipulating one of the balancing GUI controls on the GUI to modify the respective amplitude calibration parameter of the stimset corresponding to the manipulated balancing GUI control;

(v) automatically, by the programmer device, recalculating the amplitude calibration parameter of the manipulated balancing GUI control in response to (iv) and storing the recalculated amplitude calibration parameter in the stimset of the stimulation program corresponding to the manipulated balancing control; and (vi) repeating (ii)-(v) until the patient indicates that the patient experienced the stimulation sensation simultaneously during a ramp-up procedure in the at least two separate bodily regions.

* * * * *